United States Patent [19]

Acksel

[11] Patent Number: 5,534,008
[45] Date of Patent: Jul. 9, 1996

[54] SUTURING GUIDE AND CLAMP

[76] Inventor: Ione Acksel, 1267 Carlls Straight Path, Dix Hills, N.Y. 11746

[21] Appl. No.: 314,216

[22] Filed: Sep. 28, 1994

[51] Int. Cl.$^6$ .................................................. A61B 11/00
[52] U.S. Cl. ........................................ 606/148; 606/151
[58] Field of Search ................................... 606/139, 148, 606/151, 233

[56] References Cited

U.S. PATENT DOCUMENTS

| | | | |
|---|---|---|---|
| 755,921 | 3/1904 | O'Neill | 606/148 |
| 963,899 | 7/1910 | Kistler | 606/148 |
| 4,724,838 | 2/1988 | Hasson | 606/148 |
| 4,985,035 | 1/1991 | Torre | 606/167 |
| 5,242,457 | 9/1993 | Akopov et al. | 606/148 |
| 5,251,642 | 10/1993 | Handlos | 606/148 |
| 5,368,606 | 11/1994 | Marlow et al. | 606/170 |

*Primary Examiner*—Stephen C. Pellegrino
*Assistant Examiner*—Jeffrey A. Schmidt
*Attorney, Agent, or Firm*—Kenneth P. Robinson

[57] ABSTRACT

A suturing guide includes opposing guide sections having openings for guiding placement of a suturing needle. In docking a dog's ear, the suturing guide is placed in position, used as a guide for a cut and, via spaced guide openings, acts as a guide for positioning of sutures back from the edge of the cut and with desired lateral spacing. The opposing guide sections may be supported and positioned by an included, spring-biased support assembly, or may be applied independently of a support assembly. Straight and curved edge guide sections and a variety of alignment and retention features are described.

16 Claims, 4 Drawing Sheets

SUTURING GUIDE AND CLAMP

This invention relates to the suturing of body portions and, more specifically, to guides and clamps particularly suited to suturing cuts and docked ears of animals.

BACKGROUND OF THE INVENTION

For certain breeds of dogs it is traditional to dock or trim the ears, requiring suturing of the cut edge. Also, when an animal such as a horse suffers a cut it may be necessary to suture the cut to promote proper healing.

A variety of devices have been proposed as aids to accomplishing such suturing. For example, prior devices may be arranged with screw assemblies so that the device may be positioned over an ear to be docked by tightening the screw assemblies. However, such prior arrangements have typically been inconvenient and time consuming to use and have not been effective to accommodate and guide the entire process of docking and suturing or suturing alone.

It is therefore an object of the present invention to provide suturing guides and clamps characterized by one or more of the following:

a new and improved form or method of use, improved guidance of suture positioning, improved support during suturing, ease of application and removal, and enablement of guided suturing in spaced relation away from the edge of a cut.

SUMMARY OF THE INVENTION

In accordance with the invention, a suturing guide for surgical use includes first and second guide sections. The first guide section has a first surface suitable for placement against a body portion to be sutured. The first surface includes an edge extending in a first direction, and a plurality of spaced openings each extending to such edge and suitable for passage of a suturing needle. The second guide section has a second surface suitable for placement against the body portion in spaced opposed relation to the first surface of the first guide section. The second surface includes an edge extending in the first direction and a plurality of spaced openings each extending to such edge and alignable with a respective one of the spaced openings in the first surface.

The suturing guide further includes a support assembly fastened to the first and second guide sections and arranged to enable the guide sections to be respectively positioned against the body portion with the spaced openings of the first and second guide sections in spaced opposed alignment. A positioning device, such as a spring, is mechanically coupled to the support assembly and arranged to retractably urge the first and second surfaces toward each other.

In a currently preferred embodiment each of the spaced openings is the terminus of a curved opening formed in a guide section, with an entrance in a side surface and adapted to guide the positioning of a suturing needle. The respective curved openings of the first and second guide sections are thus dimensioned to provide a cooperating curved needle path on opposite sides of a body portion when the first and second guide sections are positioned in spaced alignment. In this embodiment, the support assembly includes a first portion having arm sections attached to the ends of the first guide section and a second portion having arm sections similarly attached to the ends of the second guide sections. The first and second support assembly portions are rotatably connected via an axle arrangement connecting the portions along an axis spaced from the guide sections, with a spring mechanically arranged to rotatably urge the first and second surfaces of the guide sections toward contact with each other.

BRIEF DESCRIPTION OF THE DRAWINGS

FIGS. 3A, 38, 3C and 3D are side and sectional views of portions of the FIG. 1 suturing guide.

DESCRIPTION OF THE INVENTION

Figure 1:
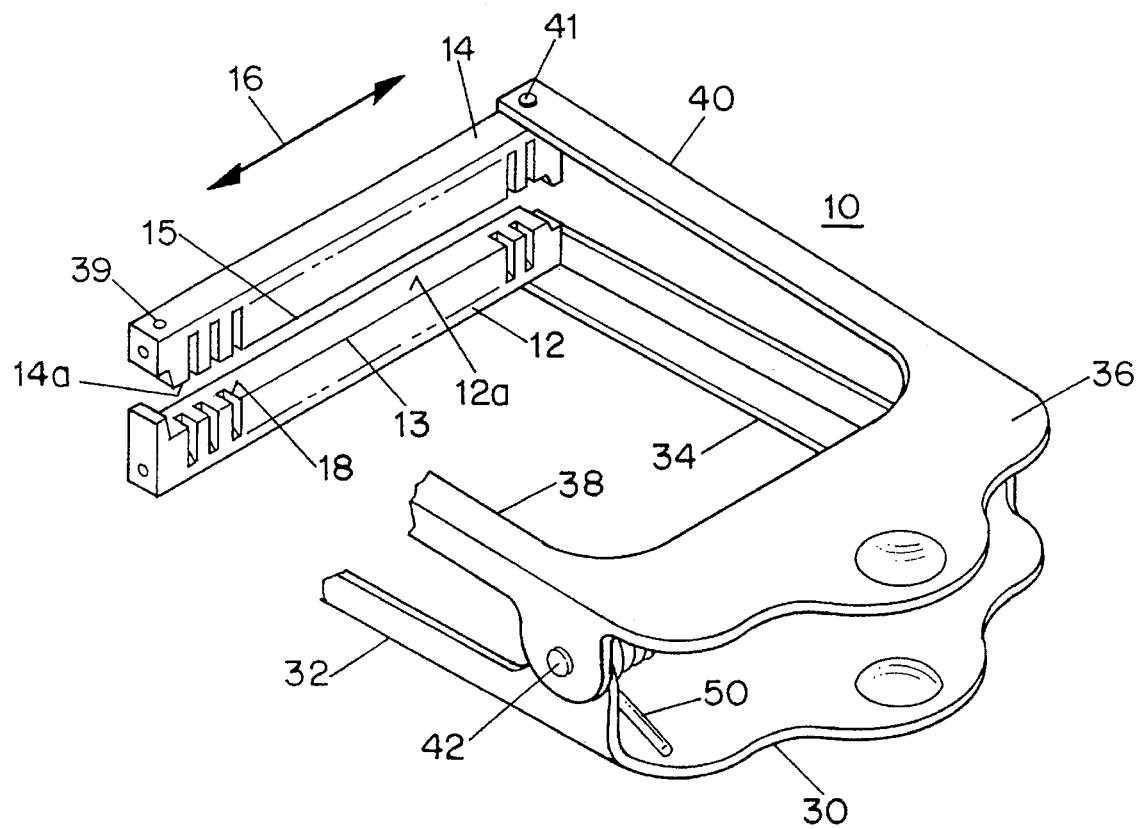
FIG. 1 is a perspective view of a suturing guide utilizing the invention.

FIG. 1 is a perspective view of a suturing guide for surgical use in accordance with the invention, with a portion removed to show details. Plan and side views of the FIG. 1 suturing guide are respectively provided in FIGS. 2A and 2B and certain details and variations will be discussed with reference to FIGS. 3A, 3B, 3C and 3D and FIG. 4.

Figure 3A:
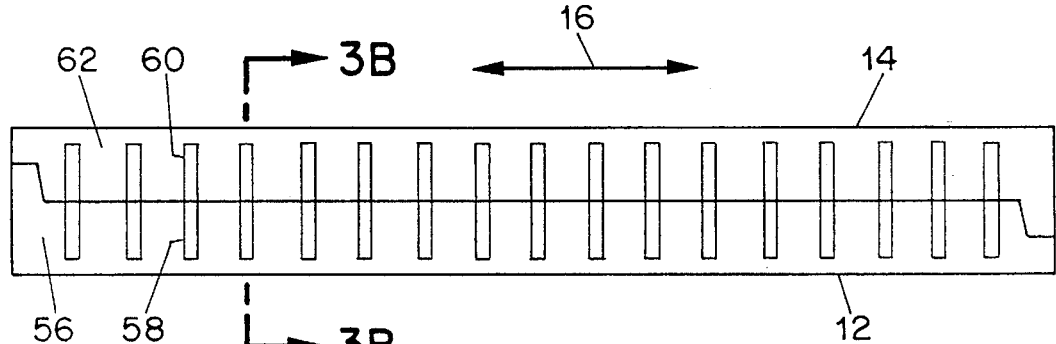

As illustrated in FIG. 1, the suturing guide 10 includes first and second guide sections 12 and 14. First guide section 12 includes a first surface 12a suitable for placement against a body portion to be sutured. As will be further described, first surface 12a of guide section 12 has an edge 13 extending in a first direction 16 and having a plurality of spaced openings 18 (see also FIG. 3C) each extending to edge 13 and suitable for passage of a suturing needle. Second guide section 14 has a second surface 14a suitable for placement against the body portion in spaced opposed relation to the first surface 12a of the first guide section 12, as illustrated in FIG. 1. Surface 14a (the bottom surface of guide section 14 in FIG. 1) is not visible in FIG. 1, however a portion of surface 14a is shown in FIG. 3D. The second surface 14a has an edge 15 extending in the first direction 16 and a plurality of spaced openings 20 (see FIG. 3D) each extending to edge 15 of second surface 14a. As illustrated in FIG. 1 (and as will be discussed further with reference to the FIG. 3A side view of guide sections 12 and 14) each of the spaced openings 20 in surface 14 is alignable with a respective one of the spaced openings 18 of the first surface 12a.

Figure 2A:
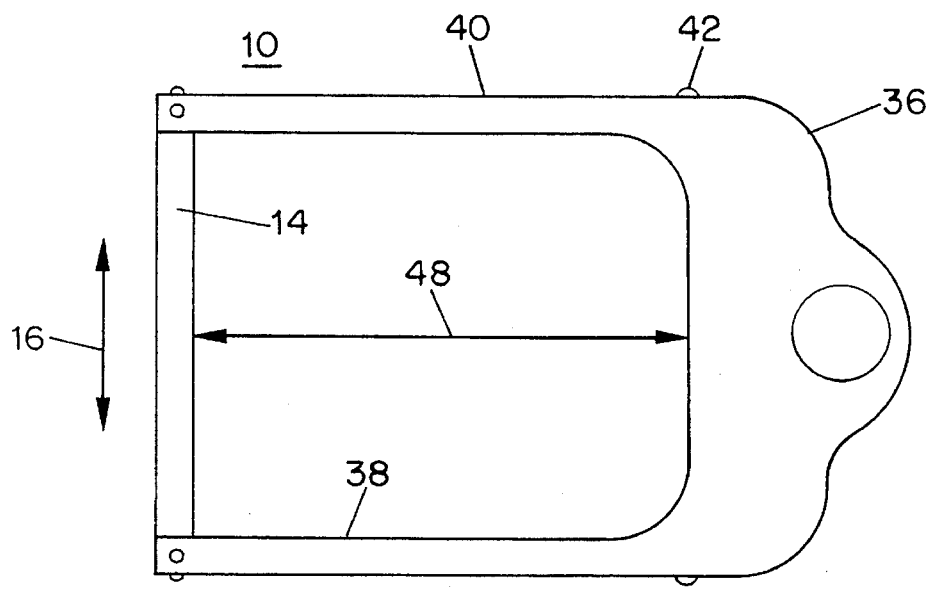
FIGS. 2A and 2B are plan and side views of the FIG. 1 suturing guide.
Figure 2B:
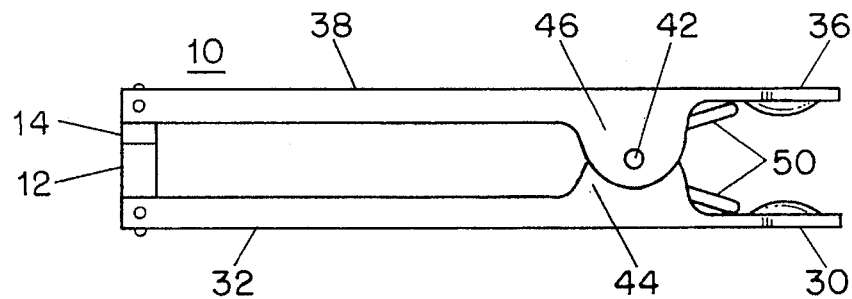

The FIG. 1 embodiment also includes a support assembly fastened to the first and second guide sections 12 and 14. As shown in FIGS. 2A and 2B, the support assembly includes a first portion 30 having arm sections 32 and 34 attached to the ends of the first guide section 12 and a second portion 36 having arm sections 38 and 40 attached to the ends of the second guide section 14. Parts of arm sections 32 and 38 are removed in FIG. 1 to provide increased visibility of guide sections 12 and 14. As shown, the arm sections each have two surfaces at right angles which are placed against top and end surfaces of guide section 14, for example, and fastened via screws or rivets, shown typically at 41, which are each placed in a hole such as indicated at 39. As illustrated, the first and second portions 30 and 36 are rotatably connected via an axle device, shown as a pin 42 with enlarged ends. Pin 42 is effective to rotatably connect the portions 30 and 36 (via openings in cooperating tab sections such as shown at 44 and 46) along an axis which extends longitudinally through pin 42 and is spaced from the first and second guide sections 12 and 14. This spacing, indicated at 48 in FIG. 2A, is specified to provide adequate room for suturing access to the openings 18 and 20 in guide sections 12 and 14. The FIG. 1 embodiment further includes a positioning device, shown as spring 50 which has a helical form extending around pin 42 for part or all of the length of the central portion of pin 42 and terminating at each end in a radially extending portion pressing against the inside of portions 30 and 36, as illustrated, in order to maintain a rotational pressure on portions 30 and 36 in known manner. Thus, positioning device 50 may comprise one or more springs supported on axle pin 42 in the manner well known in clip board construction, or other suitable arrangement as may be provided by skilled persons in order to retractably urge the first and second surfaces 12a and 14a toward contact with each other.

Figure 3B:
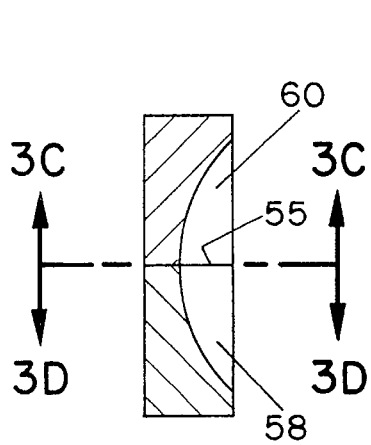
Figure 3C:
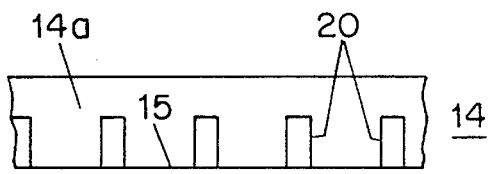
Figure 3D:
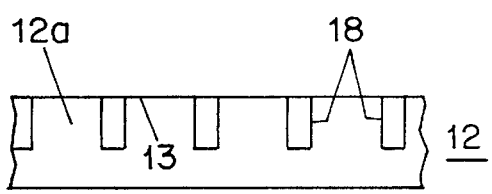
Figure 5:
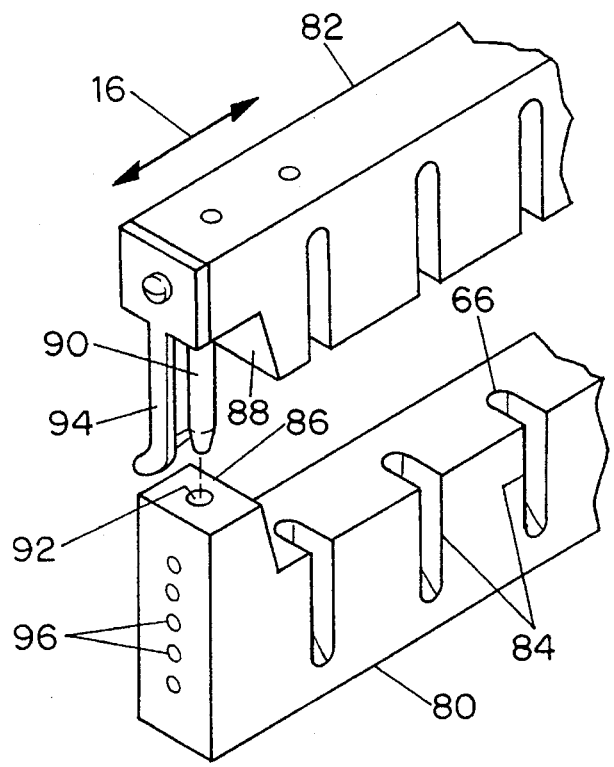
FIG. 5 is a perspective view of a portion of a third embodiment, including alignment and fastening devices.

Referring now more particularly to FIGS. 3B and 5, it will be seen that in currently preferred embodiments each of the spaced openings 18 and 20 in the surfaces 12a and 14a is the terminus of a curved opening formed in the respective guide sections 12 and 14 and adapted to guide the positioning of a suturing needle. FIG. 3A is a side view of the first and second guide sections 12 and 14 positioned together with surfaces 112a and 14a in contact with each other and each of the openings 18 respectively aligned with an opening 20. As a result, the openings 18 and 20 are not visible in FIG. 3A. FIG. 3B is a side view along cut 3B/3B in FIG. 3A with an opening 18 and an opening 20 in contiguous alignment at 55. As shown in FIGS. 3A and B, first guide section 12 has a side surface 56 extending nominally normal to the first surface 12a and opening 18 is the terminus, at surface 12a, of a curved opening 58 formed in the first guide section and from an entrance in the side surface 56. For present purposes, "nominally" indicates a relationship which is within about plus or minus 20 percent of an indicated value or relationship. Correspondingly, the second guide section 14 includes a similar curved opening extending from one of the spaced openings 20 in surface 14a to an exit in the side surface 62 of guide section 14. The respective curved openings 58 and 60 are thus dimensioned to provide a cooperating curved suturing needle path beginning on one side and continuing to the other side of a body portion which could be positioned between the two guide sections 12 and 14, when the guide sections are positioned in spaced alignment against opposite sides of a body portion. While only one pair of opposed openings in guide sections 12 and 14 have been specifically discussed, it will be appreciated that each aligned pair of curved openings shown in FIG. 3A will provide a curved path particularly suitable for suturing by use of a curved suturing needle. In FIGS. 3A–3D the openings are illustrated as having an inside squared corner profile (at 64, for example). In FIG. 5, which will be further described, the openings have an inside curved profile (at 66, for example). The particular dimensions and inside profile features of the openings can be specified by skilled persons as appropriate in particular applications.

Figure 4A:
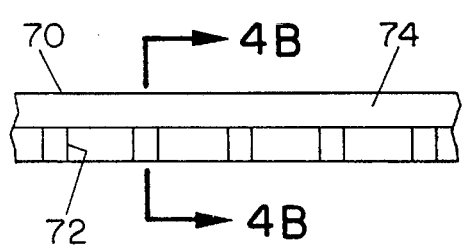
FIGS. 4A, 4B and 4C are side and sectional views of a second embodiment of the invention.
Figure 4C:
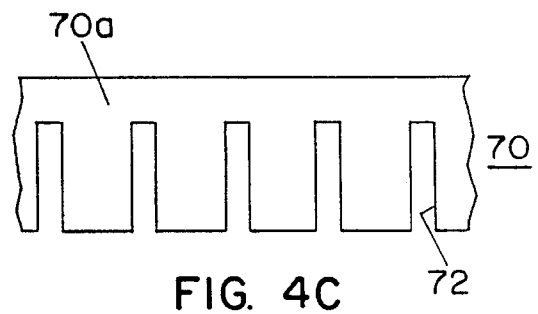
Figure 4B:
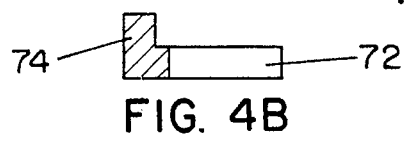

FIGS. 4A, 4B and 4C show a portion of an alternative form of a first or second guide section in accordance with the invention. The views of FIGS. 4A, 4B and 4C correspond respectively to the views of FIGS. 3A, 3B and 3C, for a single modified guide section 70. In FIG. 4B it will be seen that guide section 70 is thinner, top to bottom, than the guide sections previously discussed and the openings, shown typically at 72, are straight cuts through the guide section. With this configuration, the thinner construction permits a suturing needle to pass through opening 72 from top to bottom, rather than having a side entrance and bottom exit as discussed with reference to FIG. 3B. As shown in FIG. 4B, this configuration may include an upward extending rib 74 to provide greater stiffening of the guide section, as appropriate. In particular applications, the FIG. 4B type construction can be used for each of first and second cooperating guide sections, or a guide section of the FIG. 4B type may be paired with a cooperating guide section of the FIG. 3B type, provided the dimensions and spacings of openings 18 in surface 12a, as shown in FIG. 3C, closely correspond to the dimensions and spacings of openings 76 in surface 70a, as shown in FIG. 4C, for the two cooperating guide sections.

Referring now to FIG. 5, there are shown portions of the ends of first and second guide sections 80 and 82, which include curved openings 84 with the inside curved profile feature 66, as described. Guide sections 80 and 82 illustrate the following additional features in accordance with the invention. At 86 and 88, cooperating sections with complementary inclined surfaces are configured to aid in alignment in the direction 16. Alignment pin 90 is arranged for insertion into a corresponding alignment hole 92, in order to aid in alignment in both direction 16 and normally to direction 16. Spring finger device 94 has an inwardly extending pin arranged to extend into one of holes 96 as the guide sections 80 and 82 are urged toward contact with each other and thereby against the sides of a body portion to be sutured. The pin of spring finger device 94 is thereby effective to hold the two guide sections in a desired spaced relation, while preventing the guide sections from separating farther until the pins (one at each end of the 80/82 combination) are withdrawn from the holes. While the FIG. 1 embodiment includes the support assembly 30, 36, etc., in other applications two guide sections such as 12 and 14, 80 and 82, etc., may be utilized as a suturing guide without the inclusion of any support assembly. In such applications, arrangements such as illustrated in FIG. 5 may be employed for purposes of aligning and maintaining the two guide sections in place for suturing purposes. With an understanding of the utility of guide sections as illustrated and described in accordance with the invention, skilled persons will be enabled to implement a variety of manners and arrangements of use, which may or may not include a support assembly of the type described or modifications thereof. Where a support assembly is used, arrangements of the type shown in FIG. 5 may be included or omitted as appropriate in particular embodiments.

Figure 6:
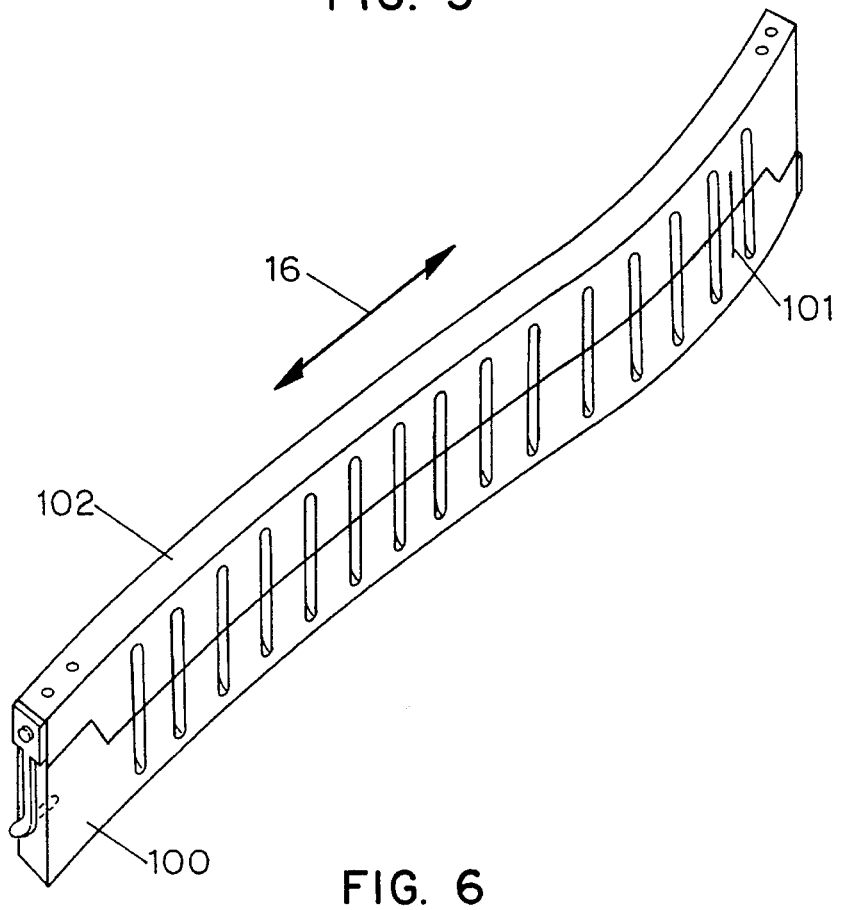
FIG. 6 is a perspective view of first and second guide sections having a curved edge pursuant to a fourth embodiment.
Figure 7:
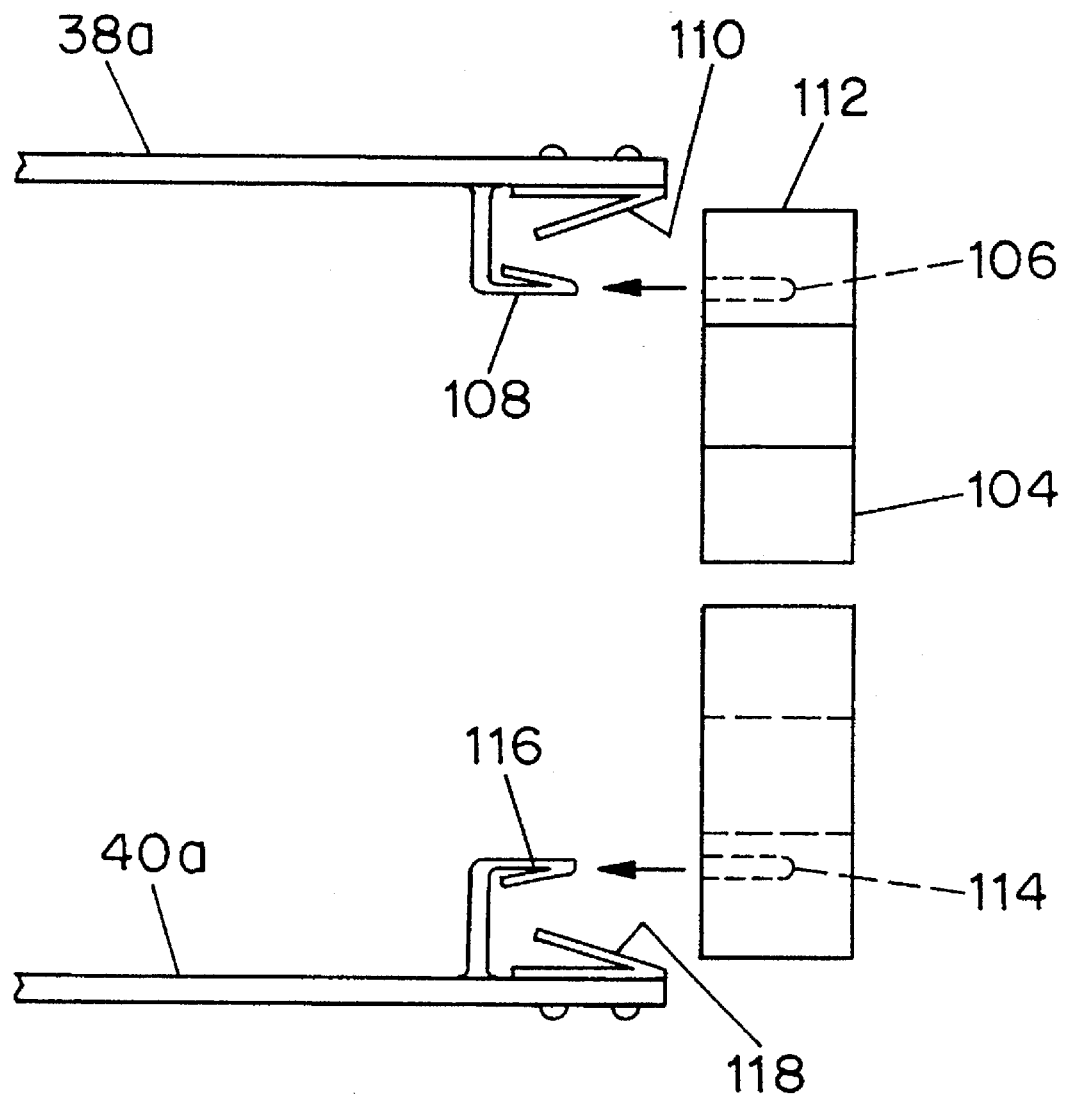
FIG. 7 shows an arrangement for fastening a support assembly to a guide section of a suturing guide.

In FIG. 6 is illustrated an embodiment of the invention wherein the first and second guide sections 100 and 102 are curved along their principal dimension which extends in direction 16. Specific configurations of this type may be particularly dimensioned in order to follow a predetermined curve, simple or complex, which is prescribed for docking the ears of a particular breed of dog. As shown at 101, reference markings may desireably be provided to enable consistent positioning so that both ears of a dog are symmetrically shaped. FIG. 7 shows in simplified form an arrangement which may be used for attaching arm sections 38 and 40, of FIG. 1, to the ends of a guide section. As illustrated in FIG. 7, guide section 104 includes fastening hole 106 and arm section 38a has a spring loaded pin 108 proportioned to enter and retain itself within hole 106. Arm section 38a also includes a spring element 110 proportioned to press against the end 112 of guide section 104 to provide a mechanical biasing force for additional structural stability after pin 108 is set in hole 106. A corresponding hole 114, pin 116 and spring element 118 combination are provided for the other end of the guide section 104. These and other mechanical arrangements may be selectively employed in embodiments of the invention.

In use, as already noted, a suturing guide in accordance with the invention may be appropriately positioned on the ear of a dog whose ear is to be docked. By use of a guide having guide sections with straight or curved edges, as desired, a cut can be made by utilizing such edge as a guide, with the cut following directly along the edge. Then, by use of a curved suturing needle carrying appropriate suturing material, suturing can be implemented by needle placement via the spaced openings in the aligned guide sections. The suturing guide need not be moved from its position and the depth of the openings back from the edge of the surface against the ear guides needle placement both as to distance from the edge of the cut and laterally from suture point to suture point along the cut. The suturing guide, in the FIG. 1 configuration for example, can then readily be removed. The guide sections may desirably be constructed of stainless steel or other appropriate material and the guide construction enables easy cleaning and sterilization, as appropriate. In other applications, suturing guides of the type described may be applied to a cut suffered by a horse, for example, by first forcing the edges of the skin adjacent the cut forward to be clamped between the guide sections of a suturing guide. With the skin adjacent the cut thus physically held, the spaced aligned openings can be utilized as discussed to position sutures at a proper distance from the edge of the cut. The suture guide can then readily be removed, cleaned and stored for future use. Once having an understanding of the invention, skilled persons will be enabled to provide suturing guides in a variety of configurations, sizes, spring strengths, etc., with and without inclusion of a support assembly, as appropriate for a large number of different applications.

While there have been described the currently preferred embodiments of the invention, those skilled in the art will recognize that other and further modifications may be made without departing from the invention and it is intended to claim all modifications and variations as fall within the scope of the invention.

What is claimed is:

1. A suturing guide for surgical use, comprising:

a first guide section including a first surface suitable for placement adjacent to a first side of a body portion, the first surface having a plurality of spaced openings each extending to an edge of the first surface and suitable for passage of a suturing needle, and wherein each of said spaced openings in the first surface is the terminus of a curved opening formed in the first guide section and adapted to guide the positioning of a curved needle;

a second guide section including a second surface suitable for placement adjacent to a second side of said body portion in spaced opposed relation to the first guide section, the second surface having a plurality of spaced openings each extending to an edge of the second surface and alignable with a respective one of said spaced openings in said first surface;

a support assembly fastened to the first and second guide sections and arranged to enable the guide sections to be respectively positioned adjacent to said first and second sides of said body portion with the spaced openings of the first and second guide sections in spaced opposed alignment; and a positioning device mechanically coupled to the support assembly and arranged to retractably urge the first and second surfaces into positions adjacent to opposite sides of said body portion.

2. A suturing guide as in claim 1, wherein the first guide section has a side surface extending nominally normal to the first surface and each curved opening includes an entrance in said side surface.

3. A suturing guide as in claim 1, wherein each of said spaced openings in the second surface is the terminus of a curved opening formed in the second guide section and the respective curved openings of the first and second guide sections are dimensioned to provide a cooperating curved needle path on opposite sides of said body portion when the first and second guide sections are positioned in said spaced alignment.

4. A suturing guide as in claim 1, wherein the first and second guide sections have the form of metallic bars having a principal first dimension and a thickness and a height normal to said first dimension, and have one of the following shapes along said first dimension: curved along the first dimension, straight along the first dimension.

5. A suturing guide as in claim 1, wherein the first and second surfaces are nominally flat surfaces.

6. A suturing guide as in claim 1, wherein the support assembly comprises a first portion having arm sections attached to ends of the first guide section and a second portion having arm sections attached to ends of the second guide section, and said first and second portions are rotatably connected.

7. A suturing guide as in claim 6, additionally comprising an axle device rotatably connecting the first and second portions of the support assembly.

8. A suturing guide as in claim 6, wherein the positioning device comprises a spring mechanically positioned to rotatably urge said first and second surfaces toward contact with each other.

9. A suturing guide as in claim 6, wherein each of the arm sections of the support assembly includes a spring-loaded pin arrangement for attachment of the arm section to a respective end of one of the first and second guide sections.

10. A suturing guide as in claim 1, wherein the first guide section includes a positioning pin for insertion into a corresponding positioning hole in the second guide section.

11. A suturing guide for surgical use, comprising:

a first guide section including a first surface suitable for placement adjacent to a first side of a body portion, the first surface having a plurality of spaced openings each extending to an edge of the first surface and suitable for passage of a suturing needle, and wherein each of said spaced openings in the first surface is the terminus of a curved opening formed in the first guide section and adapted to guide the positioning of a curved needle; and a second guide section including a second surface suitable for placement adjacent to a second side of said body portion in spaced opposed relation to the first guide section, the second surface having a plurality of spaced openings each extending to an edge of the second surface and alignable with a respective one of said spaced openings in said first surface.

12. A suturing guide as in claim 11, wherein the first guide section has a side surface extending nominally normal to the first surface and each curved opening includes an entrance in said side surface.

13. A suturing guide as in claim 11, wherein each of said spaced openings in the second surface is the terminus of a curved opening formed in the second guide section and the respective curved openings of the first and second guide sections are dimensioned to provide a cooperating curved needle path on opposite sides of said body portion when the first and second guide sections are positioned in said spaced alignment.

14. A suturing guide as in claim 11, wherein the first and second guide sections have the form of metallic bars having a principal first dimension and a thickness and a height normal to said first dimension, and have one of the following shapes along said first dimension: curved along the first dimension, straight along the first dimension.

15. A suturing guide as in claim 11, wherein the first and second surfaces are nominally flat surfaces.

16. A suturing guide as in claim 11, wherein the first guide section includes a positioning pin for insertion into a corresponding positioning hole in the second guide section.

* * * * *